United States Patent [19]

Fadda

[11] 4,067,960

[45] Jan. 10, 1978

[54] PHARMACEUTICAL COMPOSITIONS CONTAINING CARDIAC GLYCOSIDE

[75] Inventor: Carlo Fadda, Rome, Italy

[73] Assignee: R. P. Scherer Limited, England

[21] Appl. No.: 746,599

[22] Filed: Dec. 1, 1976

Related U.S. Application Data

[63] Continuation of Ser. No. 588,684, June 20, 1975, abandoned.

[51] Int. Cl.$^2$ .................. A61K 9/48; A61K 31/705
[52] U.S. Cl. .................................... 424/14; 424/182
[58] Field of Search .......................... 424/182, 14

[56] References Cited

U.S. PATENT DOCUMENTS

| | | | |
|---|---|---|---|
| 2,298,122 | 10/1942 | Hailer et al. | 424/14 |
| 2,990,333 | 6/1961 | Graham | 424/14 |
| 3,472,931 | 10/1969 | Stoughton | 424/320 |

FOREIGN PATENT DOCUMENTS

| | | |
|---|---|---|
| 2,237,619 | 2/1975 | France. |
| 2,209,526 | 9/1973 | Germany. |

OTHER PUBLICATIONS

Chiou et al., Chem. Abst., vol. 75, (1971), pp. 143,955z.

*Primary Examiner*—Sam Rosen
*Attorney, Agent, or Firm*—Allegretti, Newitt, Witcoff & McAndrews

[57] ABSTRACT

A cardiotonic dosage unit form comprises a soft gelatine capsule containing a liquid cardiotonic composition comprising (a) a cardiac glycoside, preferably digitoxin or digoxin; (b) dimethyl formamide or dimethyl acetamide; and (c) a liquid polyethylene glycol and also, optionally, (d) propylene glycol or glycerin.

The weight ratio of dimethyl acetamide or dimethyl formamide to cardiac glyceride is preferably at least 5:1 and the polyethylene glycol preferably forms at least 75% by weight of the total composition contained in the gelatine capsule.

6 Claims, No Drawings

PHARMACEUTICAL COMPOSITIONS CONTAINING CARDIAC GLYCOSIDE

This is a continuation of application Ser. No. 588,684, filed June 20, 1975, now abandoned.

This invention is concerned with improvements in and relating to pharmaceutical compositions and, more particularly, relates to cardiotonic compositions containing, as active ingredient, a cardiac glycoside derived from *Digitalis purpurea* or *Digitalis lanarta* or a derivative thereof. For the sake of convenience such materials will hereinafter be simply referred to as "cardiac glycosides".

Cardiac glycosides are widely used cardiotonic agents and are commonly formulated as tablets for oral administration. Of necessity, each tablet must contain a very small amount of the active ingredient, (e.g. 250 micrograms or less) since these particular active agents are administered in such very small doses, almost always less than 0.5 mg. The fact that each tablet has to contain so little of the active ingredient gives rise to problems in formulation and, in particular, makes it very difficult to ensure perfect compounding of the tableting mix so that each tablet contains the same amount, with tolerable limits, of the active ingredient, (see, for example, Thomas et al, The Lancet, December 1, 1973, pp 1267-8; Fraser et al, 5, Pharm. Pharmac., 1973, 25, pp 268-973; and Shaw et al, British Medical Journal, 1973, 4, pp 763-766).

It is an object of the present invention to provide an improved dosage unit suitable for the oral administration of a cardiac glycoside.

Accordingly, the present invention provides a cardiotonic dosage unit form comprising a soft gelatine capsule containing a liquid cardiotonic composition comprising
 a. a cardiac glycoside;
 b. dimethyl formamide or, preferably, dimethyl acetamide; and
 c. a liquid polyethylene glycol; and, optionally also
 d. propylene glycol or glycerine.

The cardiac glycoside used in the compositions of the invention may be, for example, digoxin, digitoxin, digitalin, lanatoside C, acetyl digitoxin, acetyl digoxin or methyl digoxin. The most generally preferred cardiac glycosides are digitoxin and digoxin, especially the latter.

The compositions in accordance with the invention will generally be prepared by dissolving the cardiac glycoside in the dimethyl acetamide or dimethyl formamide. The weight ratio of dimethyl acetamide to dimethyl formamide to cardiac glycoside is usually 5:1 or higher, e.g. from 5:1 to 15:1 by weight preferably forming less than 25% by weight of the total water/ethanol mixture. Suitably the weight ratio of water/ethanol mixture of cardiac glycoside is of the order of about 80:1 or even higher.

The solution of cardiac glycoside is mixed with the polyethylene glycol (optionally containing propylene glycol or glycerine) and the polyethylene glycol forms the major component of the compositions of the invention generally being present in the amounts of at least 75% by weight, preferably from 80-95% by weight, of the total composition contained in the soft gelatine capsule.

The gelatine capsule will be one formed of gelatine containing a plasticiser such as glycerine, propylene glycol, diethylene glycol or hexanetriol. Further, the plasticiser may comprise one of those mentioned above together with sorbitol in order to improve the properties of the capsules with respect to exposure to moisture containing atmospheres. The amount of sorbitol will preferably be about equal to the amount of glycerin or other plasticiser. Accordingly, a preferred capsule comprises gelatine plasticised with from about 8 to 15% by weight of glycerin preferably about 12.5% by weight, and from 12.5 to 15% by weight of sorbitol preferably about 13.5% of sorbitol, the percentages being based on the total weight of gelatine glycerine and sorbitol.

The total weight of ingredients contained in the gelatine capsule of the compositions of the invention is suitably from about 100 to 300 milligrams, and, clearly, the weight of cardiac glycoside contained in each capsule will be that generally required for a unit dose, for example from 50 to 300 micrograms.

The compositions of the invention are prepared in the liquid phase so that it is possible to obtain accurate and consistent dispersion of the active ingredient (cardiac glycoside) throughout the liquid phase of the composition. Accordingly, it is possible to ensure that each dosage unit (i.e. capsule) contains the same amount (within tolerable limits) of the active ingredient.

It has also been found, that the unit dosage forms of the invention give better or more rapid availability of the active ingredient (as indicated by release tests carried out in artificial gastric juices) than do comparable tablets. Thus, it has been found not only do the capsules of the invention give a more rapid release of their contents but also that they give a more complete release of their content than do the tablets which frequently release only about 50% or less of their contents. It will be appreciated, therefore, that the capsules of the invention constitute a much more reliable dosage unit than do many tablets since they can be relied upon to release substantially all of their active ingredient content within a relatively short period of time whereas this is not the case with tablets.

In order that the invention may be well understood the following examples of formulations for 140 and 280 milligram capsules are given by way of illustration only.

Example 1
140 Mg capsule containing 131 micrograms of digoxin

| | |
|---|---|
| Digoxin | 0.131 mg |
| Dimethyl acetamide | 0.75 mg |
| PEG 400 | 140.119 mg |

Example 2
140 Mg capsule containing 66 micrograms of digoxin

| | |
|---|---|
| Digoxin | 0.066 mg |
| Dimethyl acetamide | 0.75 mg |
| PEG 400 | 140.559 mg |

Example 3
140 Mg capsule containing 263 micrograms of digoxin

| | |
|---|---|
| Digoxin | 0.263 mg |
| Dimethyl acetamide | 4.500 mg |
| PEG 400 | 139.237 mg |

I claim:

1. A cardiotonic dosage unit form comprising a soft elastic gelatin capsule containing a solution of (a) about 50 – 300 micrograms of a digitalis cardiac glycoside including digoxin, digitoxin, digitalin, lanatoside C, acetyl digitoxin, acetyl digoxin or methyl digoxin, (b) dimethyl formamide or dimethyl acetamide, the weight ratio of dimethyl acetamide or dimethyl formamide to said cardiac glycoside being at least 5:1 and (c) liquid polyethylene glycol comprising at least 75% by weight of the total solution contained in said gelatin capsule, the total solution having a weight of about 100 – 300 milligrams.

2. The composition of claim 1 including propylene glycol or glycerin.

3. The composition of claim 1 wherein said cardiac glycoside is digoxin.

4. The composition of claim 1 wherein said cardiac glycoside is digitoxin.

5. The composition of claim 1 wherein the weight ratio of dimethyl acetamide or dimethyl formamide to said cardiac glycoside is about 5:1 to 15:1.

6. The composition of claim 1 wherein said polyethylene glycol forms about 80 – 95% by weight of said solution.

* * * * *